(12) United States Patent
Swart et al.

(10) Patent No.: US 7,797,989 B2
(45) Date of Patent: Sep. 21, 2010

(54) SAMPLE INJECTOR, IN PARTICULAR FOR HIGH-POWER LIQUID CHROMATOGRAPHY

(75) Inventors: Remco Swart, Bussum (NL); Guillaume Tremintin, Sixt sur Aff (FR)

(73) Assignee: Dionex Softron GmbH, Germering (DE)

( * ) Notice: Subject to any disclaimer, the term of this patent is extended or adjusted under 35 U.S.C. 154(b) by 314 days.

(21) Appl. No.: 11/996,069

(22) PCT Filed: Dec. 1, 2006

(86) PCT No.: PCT/DE2006/002140

§ 371 (c)(1), (2), (4) Date: Jan. 17, 2008

(87) PCT Pub. No.: WO2007/062642

PCT Pub. Date: Jun. 7, 2007

(65) Prior Publication Data
US 2008/0229810 A1    Sep. 25, 2008

(30) Foreign Application Priority Data
Dec. 1, 2005   (DE) ................ 10 2005 057 463

(51) Int. Cl.
*G01N 30/22* (2006.01)
*G01N 1/00* (2006.01)
(52) U.S. Cl. .................. 73/61.56; 73/863.45
(58) Field of Classification Search ............. 73/23.42, 73/61.55, 64.56, 863.41, 863.45
See application file for complete search history.

(56) References Cited
U.S. PATENT DOCUMENTS
4,957,009 A * 9/1990 Nohl et al. ............ 73/864.84
5,637,787 A   6/1997 Fukushima et al.
5,814,742 A   9/1998 Vissers et al.

(Continued)

FOREIGN PATENT DOCUMENTS
JP   2005 265805 A   9/2005

OTHER PUBLICATIONS
Swart, et al. "Fully Automated Off-line Multidimensional LC Methods in Proteomics," HPLC 2006: 30th Int. Symp. High Performance Liquid Phase Separations (Jun. 17, 2006-Jun. 23, 2006), 4 pages.

(Continued)

*Primary Examiner*—John Fitzgerald
(74) *Attorney, Agent, or Firm*—The Culbertson Group, P.C.

(57) ABSTRACT

A device for feeding samples to a separating device and for collecting sample fractions generated by means of the separating device, especially for high-performance liquid chromatography, with a first switch valve unit, which has at least eight ports and two switch positions. The device has a dosing device for feeding a sample to the switch valve unit, which is connected to a suction port of the first switch valve unit and which interacts with a removal and discharge device for the removal of a sample from at least one sample-holding container and for the discharge of each fraction into one of several fraction-holding containers, which is connected to a suction and discharge port of the first switch valve unit. The device uses a single switch valve unit configured in a new way to replace the function of two switch valve units, resulting in significantly simpler and cheaper construction.

18 Claims, 8 Drawing Sheets

U.S. PATENT DOCUMENTS

| | | | |
|---|---|---|---|
| 6,502,448 B1* | 1/2003 | Rapkin | 73/1.03 |
| 6,874,354 B2* | 4/2005 | Cueni et al. | 73/61.55 |
| 6,989,129 B2* | 1/2006 | Licklider et al. | 422/70 |

OTHER PUBLICATIONS

Vissers, et al., "Two-Dimensional Capillary Liquid Chromatography Based on Microfractionation," Journal of Microcolumn Separations, vol. 11, No. 4 (Mar. 11, 1999), 10 pages.

Sandra, et al. "Comprehensive pSFCxpSFC-MS for the Characterization of Triglycerides in Vegetable Oils," LC-GC Europe (Dec. 2, 2003), 4 pages.

Bushey et al., "Automated Instrumentation for Comprehensive Two-Dimensional High-Performance Liquid Chromatography of Proteins," Analytical Chemistry, American Chemical Society, vol. 62, No. 2 (Jan. 15, 1990), 7 pages.

Dragan et al., "A Proteome Analysis Involving Off-line 2D-LC of Intact Proteins, Proteolytic Digestion and Capillary RP-LC-MS/MS Analysis," HPLC 2005: 29th Symp. High Performance Lquid Phase Separations, Stockholm, Sweden (Jun. 26, 2005), 2 pages.

Mitulovic et al. "Automated, on-line two dimensional nano liquid chromatography tandem mass spectrometry for rapid analysis of complex protein digests," Proteomics. vol. 4, No. 9 (Sep. 2004), 14 pages.

Machtejevas et al., "Automated multi-dimensional liquid chromatography: sample preparation and identification of peptides from human blood filtrate," Journal of Chromatography B: Biomedical Sciences & Applications, Elsevier, vol. 803, No. 1 (Apr. 16, 2004), 10 pages.

Gilson, Inc. product brochure, "233 XL System for On-Line Column Switching", especially page 3, Middleton, WI, U.S.A. (12 pages) 1998.

LC Packings, "Application Note Famos μ-Sampling Workstation, nr. 10: Appendix I: 2-D Capillary LC Separations" (1 page) Sep. 1998.

* cited by examiner

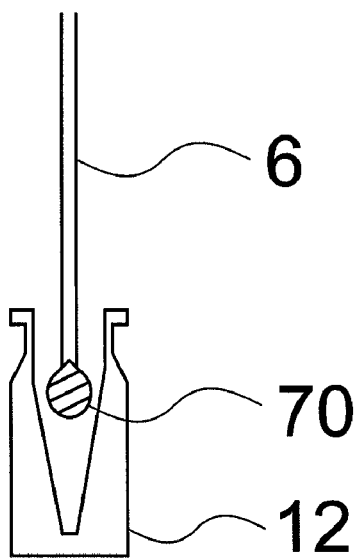
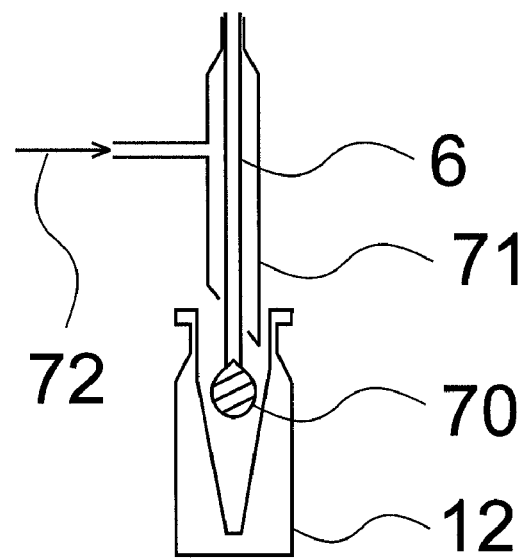
Fig. 4a
Fig. 4b

SAMPLE INJECTOR, IN PARTICULAR FOR HIGH-POWER LIQUID CHROMATOGRAPHY

TECHNICAL FIELD

The invention relates to a device for feeding samples to a separating device and for collecting sample fractions generated by the separating device, especially for high-performance liquid chromatography (HPLC).

BACKGROUND OF THE INVENTION

In liquid chromatography, a compound is broken down into its components in a chromatographic column, so that these components can be analyzed or further processed.

For the analysis of complex compounds, e.g., peptides or proteins, there is frequently the problem that the separating power is not sufficient to be able to distinguish or selectively analyze the individual components. Therefore, for such compounds, several separating steps are used one after the other. Here, it is especially efficient to use different material properties for the individual separations. In this way, the compound can first be broken down into substance groups, which can then be analyzed individually in more detail. Such methods are known as so-called two-dimensional, three-dimensional, or multi-dimensional chromatography methods (2D or 3D chromatography).

Here, one distinguishes between online methods, in which the separating steps follow one another directly in time, as well as offline techniques, in which the separating steps are performed independently of each other in time. The latter has the advantage that the individual separating steps can be optimized individually and independently of each other.

However, offline techniques require higher expense because the components (fractions), already separated in the preceding steps, must be buffered in separate form in order to be able to feed them to the following separating processes at the given time. The process is designated as fractioning. The collection of the fractions is usually performed with a separate device, the fraction collector. This divides the fractions into a corresponding number of fraction collecting or holding containers.

Usually, one would like to collect a certain, preset liquid volume in each fraction-collecting container.

Automated analysis systems usually have available automatic sample injectors, which hold a plurality of samples to be analyzed and which can feed these in series according to the analysis system. Such a sample injector is described, for example, in U.S. Pat. No. 5,814,742. Because such sample injectors form the basis of both the invention and the state of the art, the components are explained with reference to the simplified, schematic representation in FIG. 1.

Through the input capillary 1, the liquid flow delivered by a pump is led into the sample injector and leaves it via the output capillary 5. Here, a chromatographic separating column is connected, which is designated below as column 20. This is usually located outside of the sample injector. In the liquid flow there is a 6-port switch valve 2, which has available two switch positions. The position shown in FIG. 1 is designated below as "position a-b," where the port a is connected to b, c to d, and e to f. The second position is designated as "position f-a" and connects port b to c, d to e, and f to a. Thus, the liquid flow from the input capillary 1 can directly pass the switch valve b. The sample containers 7 contain the samples to be analyzed, which can be removed via a sample needle 6. A mechanism not shown in FIG. 1 allows the sample needle 6 and the sample container 7 to move relative to each other, so that the sample needles 6 can approach any sample container 7 and can be inserted into this container in order to remove the appropriate sample.

In the shown position a-b of the switch valve 2, the following components are connected in series: a dosing syringe 4, a sample loop 3, a connection capillary 8, and also the sample needle 6. While the sample needle 6 is inserted into a sample container 7, sample material can be removed from the sample container 7 through suction with the dosing syringe 4 and can be drawn, in particular, into the sample loop 3. By switching the switch valve 2 to position f-a, the sample loop 3 between the input capillary 1 and the output capillary 5 is switched and the sample material is transported with the liquid flow in the direction towards the column 20. Adding the sample into the liquid flow is designated as injection. In this described way, the samples to be analyzed can be injected in any sequence. During the injection, the dosing syringe 4 is now connected directly to the sample needle 6. In order to empty the dosing syringe again, the sample needle 6 can be moved to a waste port 9, which receives the excess solution and feeds it to a container for waste.

Furthermore, automatic sample injectors usually contain devices in order to clean the sample needle 6 from any adhering residue of the stored sample. These are not shown in FIG. 1 for the sake of clarity. In this way, diverting sample material from one sample container 7 to the next should be avoided.

The injection principle described above has the disadvantage that not only the sample loop 3, but also at least the sample needle 6 and the capillary 8 must be filled with sample material. In this way, considerably more sample material is needed than is required for the injection. Another disadvantage is that the sample amount to be injected is fixed by the size of the sample loop. Indeed, it would be possible, in principle, to draw the syringe 4 so far that the sample loop 3 is only partially filled with sample material, but this requires, e.g., exact knowledge of the volume of the capillary 8 and the sample needle 6.

These two disadvantages can be avoided through the so-called "micro-liter pickup" method, which is also described in U.S. Pat. No. 5,814,742. Here, one of the sample containers 7 contains a transport liquid, i.e., solution without sample material. Before suctioning the sample, a certain amount of this transport liquid is suctioned from this container. Then the sample needle 6 is moved into the sample container 7, which contains the desired sample. Now only the desired, small amount of sample is suctioned, wherein, in each case, its volume must be smaller than the interior volume of the sample loop 3. Then the sample needle is again moved into the container with transport liquid and this is sufficiently suctioned so that the "sample plug" enclosed between transport liquid is located in the sample loop 3. In this method, no sample material is lost and small sample volumes can also be injected, which are significantly less than the interior volume of the sample loop.

In principle, a sample injector can also be used for sample fractioning, since the sample injector already has available a holding device for sample containers and a corresponding positioning ability for the sample needle. Thus, the necessary components for distributing the fractions to a number of fraction-collecting containers are already present. Corresponding solutions have been published, for example, in:

LC Packings, Baarsjaweg 154, 1057 HM Amsterdam, Netherlands: Application Note FAMOS µ-Sampling Workstation, No. 10, Appendix I: "2-D capillary LC separations," and Gilson Inc., Middleton, Wis. 53562-0027, USA: Product Brochure 233 XL System for On-Line Column Switching, pg. 3: "Fraction collection in sealed vials . . . ."

These known solutions differ from each other through device-specific features, for example, in construction; however, all require an additional switch valve for switching between the sample injecting and fraction collecting functions. Because such switch valves are very expensive due to the strict requirements, this means considerable additional expense.

Such a solution is shown schematically in FIG. 2 for better understanding of the present invention:

The first separating step is performed in column 20, i.e., the collecting fractions are sequentially discharged at the output of the column 20. These fractions can now be distributed to a number of fraction-collecting containers.

For this purpose, the sample injector as shown in FIG. 2 must be expanded. Here the connection capillary 8 is separated into two connection capillaries 801 and 802 and a second switch valve 13 is inserted in-between. The fractions discharged from the column 20 are led back into the sample injector via the return capillary 10 and can be fed to the fraction-collecting containers 12 via the second switch valve 13, the connection capillary 801, and the sample needle 6. The waste capillary 11 leads to a waste container, in which the solution coming before or after the arrival of the fractions, as well as undesired fraction components, can be collected. According to the position of the second switch valve 13, the arrangement works either as a sample injector or as a fraction collector.

The operation is as follows: first both switch valves 2 and 13 are in position a-b, as shown in FIG. 2. A sample is removed from the sample container in the way as described above and injected by switching the switch valve 2. It is led into the column 20 via the outlet capillary 5, where the first separating step is performed. Passing through the capillaries and the separation itself take a certain amount of time, so that the separated fractions reach the sample injector at a later time via the return capillary 10. Now the sample needle 6 is positioned on the desired fraction-collecting container 12 and the second switch valve 13 is switched to position f-a, so that the return capillary 10 is connected to the sample needle 6 via the connection capillary 8. The fraction is stored in the corresponding fraction-collecting container 12. For the next fraction, the sample needle 6 is positioned on the next fraction-collecting container 12.

SUMMARY OF THE INVENTION

Therefore, starting from this state of the art, the present invention provides a device for feeding samples to a separating device and for collecting sample fractions generated by means of the separating device, especially for high-performance liquid chromatography, which features a simpler and more cost-effective construction.

The invention works according to the principle that by using a switch valve unit with at least eight ports and two switch positions, it is possible to devise such a device with merely a single switch valve unit, which results in a significantly simpler and more cost-effective construction relative to the prior art.

In addition, the invention makes it possible to upgrade existing simple sample injectors to combination sample injectors/fraction collectors.

According to a preferred embodiment of the invention, the first switch valve unit (201) has a controllable drive, which is controlled by a control unit, so that the first switch valve unit is located in the first switch position during a sample suction phase, wherein a sample is transported from a sample-holding container into the sample reservoir by means of the removal and discharge device during the sample suction phase; so that the first switch valve unit is set to the second switch position after the sample suction phase, wherein, in this sample injection phase following the sample suction phase, the sample is fed from the sample reservoir to the first separating device via the separating device transfer port by means of the solution fed via the solution feed port, and the medium coming from the first separating device is fed via the separating device transfer port to the waste port of the first switch valve unit; and so that the first switch valve unit is set to the first switch position after the sample injection phase, wherein, in this first separating phase after the sample injection phase, solution is further fed to the first separating device, and the medium fed from the output port of the first separating device to the separating device transfer port of the first switch valve unit is fed via the suction and discharge port of the first switch valve unit to the removal and discharge device and discharged from this device in the form of several fractions into corresponding fraction-collecting containers.

The control unit here can set the removal and discharge device and/or the sample-holding container from which a sample is to be removed into a position in which a sample can be removed from the desired sample-holding container before the sample suction phase.

In addition, the control unit can move the removal and discharge device and/or a waste port during the injection phase into a position in which the medium coming out of the removal and discharge device is fed to the waste port. In this way, liquid that is located in the lines or the separating device but that contains no components to be analyzed can be discharged.

The control unit can successively set the removal and discharge device and/or the fraction-collecting containers into several fraction discharge positions during the separation phase, wherein medium coming from the removal and discharge device is fed as a fraction to the relevant fraction-holding container in each fraction discharge position. In this way, the fractioning process can be automated.

According to another embodiment of the invention, there is a second switch valve unit, which connects the separating device transfer port of the first switch valve unit to the input port of the first separating device in a first switch position and, in a second switch position, to an input port of a second separating device for a second separating phase, between the separating device transfer port of the switch valve unit and the input port of the first separating device. In this way, 2D separation can be realized with automatic fractioning according to the first dimension (i.e., the first separating phase).

Here, the second switch valve unit can have a controllable drive and the control unit can set the second switch valve unit into the second switch position for performing the second separating phase.

In this position of the second switch valve unit, the control unit controls the drive of the first switch valve unit for performing the second separating phase so that, preferably, the first switch valve unit (201) is located in the first switch position during the sample suction phase for the second separating stage, wherein, during the sample suction phase, a sample is transported from a fraction-holding container into the sample reservoir by means of the removal and discharge device and so that the first switch valve unit is set into the second switch position after the sample suction phase, wherein, in this sample injection phase following the sample suction phase, the sample is fed to the second separating device from the sample reservoir via the separating device transfer port of the first separating device and the second switch valve unit by means of the solution fed via the solution feed port for the second separating phase.

According to a preferred embodiment of the invention, the second switch valve unit has the features of Claim 10. This gives the possibility of using a second solution in a simple way for the second dimension, i.e., the second separating phase, as is necessary in many cases for separation according to different material properties.

For performing a second separating phase, the control unit controls the drives of the first and second switch valve units preferably so that the first switch valve unit is located in the first switch position during the sample suction phase, wherein a sample is transported from a fraction-holding container into the sample reservoir by means of the removal and discharge device during the sample suction phase, so that after the sample suction phase the first switch valve unit is set to the second switch position and the second switch valve unit is set to the second switch position, wherein, in this sample injection phase following the sample suction phase, the sample is fed to the sample injection port of the second switch valve unit from the sample reservoir via the separating device transfer port of the first switch valve unit by means of the solution fed via the solution feed port of the first switch unit and to the input port of the second separating device via the separating device transfer port of the second switch valve unit, and so that after the sample injection phase the second switch valve unit is set back to the first switch position, so that the second solution is fed via the solution feed port of the second switch valve unit and the separating device transfer port of the second switch valve unit to the input port of the second separating device.

According to another embodiment of the invention, a sample-concentrating unit can be connected before the second separating device. In this way, it is possible to concentrate low concentration samples of relatively large volume into highly concentrated samples of small volume and then further separate and analyze them.

The sample-concentrating unit can comprise a retaining unit and a third switch valve unit, wherein the retaining unit and the third switch valve unit are connected, so that in a second switch position of the third switch valve unit, the medium fed to the second separating device and containing the sample is led through the retaining unit, wherein the retaining unit allows the passage of essentially only the solution and blocks the components of the sample; and so that in a first switch position, a second solution fed to the sample-concentrating unit flows through the retaining unit in the reverse direction, which flushes sample components concentrated on the retaining unit and transports these components to the second separating device.

The third switch valve unit here preferably has a controllable drive and is controlled by the control unit, so that during the sample injection phase, the third switch valve unit is set into the second switch position and the second switch valve unit is set into the second switch position, and so that in the second separating phase following the sample injection phase, the third switch valve unit is set at the first switch position.

According to another embodiment of the invention, in place of the third switch valve unit, a fourth switch valve unit can be provided, which connects, in a first switch position, the output port of the first separating device and, in a second switch position, the output port of the second separating device to the separating device transfer port of the first switch valve unit. In this way, fractioning according to two dimensions (separating phases) is possible.

Additional embodiments emerge from the subordinate claims, the detailed description, and the drawings.

The invention is explained in more detail below with reference to the figures shown in the drawings.

BRIEF SUMMARY OF THE DRAWINGS

FIG. 4 is a schematic representation of two variants for dripping a fraction from the sample needle.

DETAILED DESCRIPTION OF PREFERRED EMBODIMENTS

Figure 3:
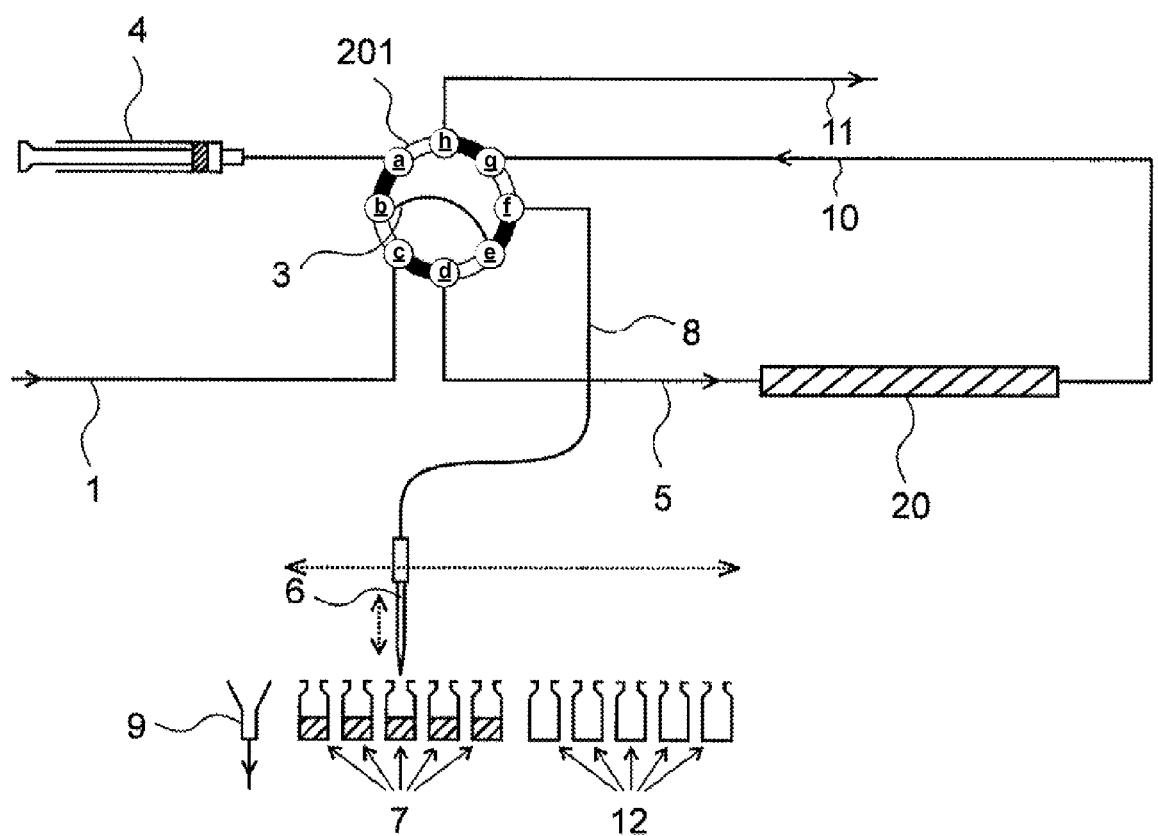
FIG. 3 is a schematic representation of a first embodiment of a device according to the invention.

FIG. 3 shows a schematic representation of a first embodiment of an arrangement according to the invention for a combination sample injector/fraction collector, in which only the components necessary for explaining the basic functionality are shown.

Figure 1:
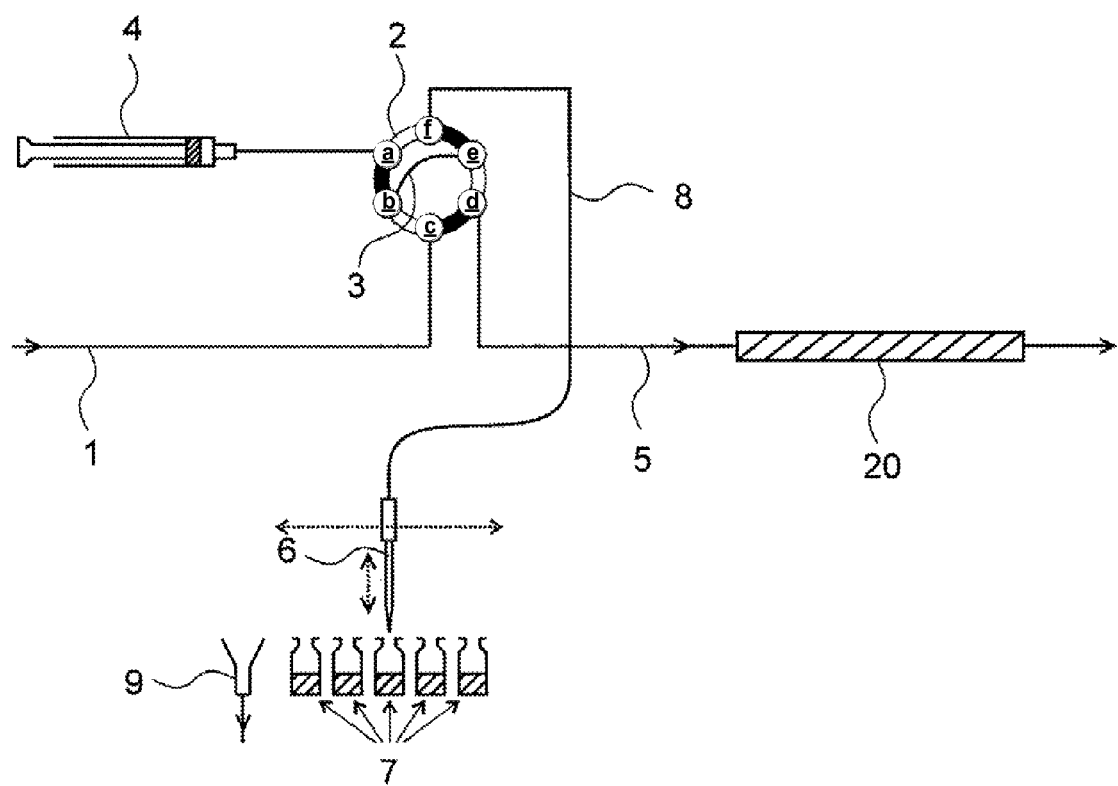
FIG. 1 is a schematic representation of the basic principle of a known automatic sample injector.
Figure 2:
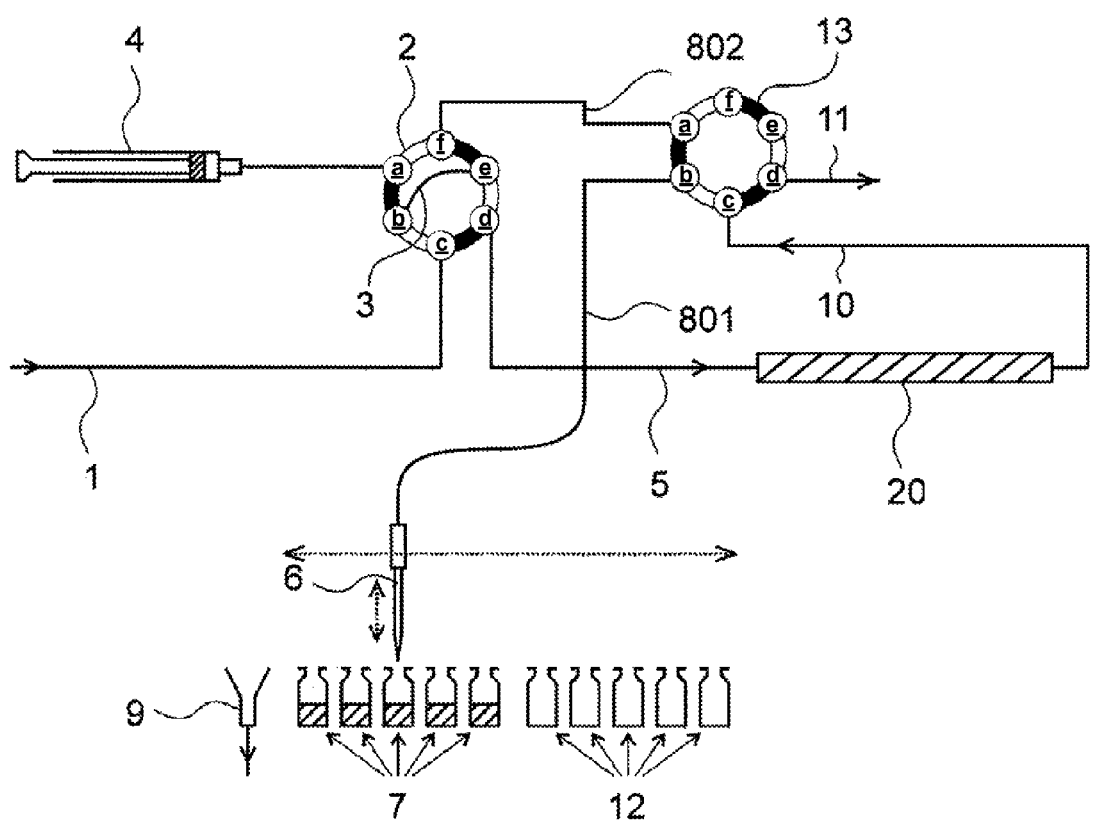
FIG. 2 is a schematic representation of a known sample injector expanded for fractioning samples.

The 6-port switch valve 2 of the sample injector according to FIG. 2 is replaced with an 8-port switch valve 201. The switch valve 13 also necessary in the device in FIG. 2 is eliminated.

Analogous to the description of the 6-port valve in FIG. 2, the two switch positions of the 8-port valve are designated below with the reference symbols a-b and h-a.

The connections of the ports a to f of the 8-port valve in FIG. 3 correspond exactly to the connections in the device shown in FIG. 2. The return capillary 10 is connected to port g and is connected to the waste capillary 11 in position a-b of the switch valve 201.

The function of the port a to f of the 8-port switch valve 201 is identical to the corresponding ports of the 6-port switch valve 2 according to the state of the art from FIG. 2. In this respect, the function is also analogous to the state of the art:

In the shown position a-b of the switch valve 201, the following components are connected in series: the dosing syringe 4, the sample loop 3, the connection capillary 8, and also the sample needle 6. While the sample needle 6 is inserted into a sample container 7, sample material can thus be removed from the sample container 7 by suctioning with the dosing syringe 4 and suctioned, in particular, into the sample loop 3.

By means of the newly added ports g and h relative to the state of the art, the return capillary 10 is connected to the waste capillary 11. Thus, the liquid flow, which comes back from the column 20 and which, at this point, still contains no fractions to be collected, is fed to the waste.

Before injection, the sample needle 6 can be moved to the waste port 9 in order to prevent the liquid flow discharged from the sample needle 6 from entering into the sample container 7 during injection.

For the injection, the switch valve 201 is then switched into position h-a, so that the sample loop 3 is connected between the input capillary 1 and the output capillary 5 and the sample material is fed to the column 20. The first separating step takes place there.

Furthermore, in position h-a of the switch valve 201, the dosing syringe 4 is connected directly to the waste capillary 11 for emptying the syringe in this position.

After injection, the switch valve 201 can be switched back selectively into position a-b or can remain in position h-a. In both cases, the liquid flow is led from the input capillary 1 into the output capillary 5, either directly or indirectly via the sample loop 3. The liquid flow arriving via the return capillary 10 is fed to a container for waste either via the waste capillary 11 or the waste port 9.

The method described in the state of the art for processing small quantities of samples (micro-liter pickup) can also be used in connection with the invention. For this purpose, only the suctioning of the sample as described there must be performed.

After injection, the injected sample material passes through the capillary 5 and reaches the column 20. The transit time through the columns varies according to the material properties, so that the individual components appear at the output of the column separated in time. Passage through the capillaries and the separation itself take a certain amount of time, so that the separated fractions reach the sample injector via the return capillary 10 with significant delay (relative to the injection).

Before the fractions to be collected arrive, the residue of the stored sample must be removed from the sample needle 6 and the connection capillary 8. For this purpose, the sample needle can be positioned on the waste port 9, and the switch valve 201 can be brought into position h-a. The liquid flow arriving via the return capillary 10 now transports the undesired sample residue into the waste port 9.

As soon as the fractions separated in the column 20 arrive via the return capillary 10, the sample needle 6 is positioned on the desired fraction-collecting container 12 and the switch valve 201 is switched to position h-a, so that the return capillary 10 is connected to the sample needle 6 via the connection capillary 8.

At the end of the sample needle 6, a liquid drop is formed, which contains the desired fraction and is to be deposited in the corresponding fraction-collecting container 12, as soon as it contains the desired, preset liquid volume. How this can be achieved is described farther below.

For the next fraction, the sample needle 6 is positioned on the next fraction-collecting container 12.

During the positioning process, the next liquid drop which already contains the fraction to be deposited in the next fraction-collecting container 12 forms at the end of the sample needle 6. The flow rate delivered via the input capillary 1 must be selected to be low enough that the liquid drop does not already drip during the positioning process.

The number of fractions to be preferably collected is a function of the period of the separating process. If the number is too low, the advantage of fractioning is largely lost. If the number is too high, the sample quantity collected per fraction is too small for a second separation step.

Values preferred in practice were the collection of, for example, 20 samples over a time period of, for example, 20 minutes.

At this point, it shall be mentioned that the control of all of the switch valves and also of the sample needle 6 relative to the sample containers 7 or the fraction containers 12 can be performed preferably in a partially or completely automated way. For this purpose, the switch valves (switch valve units) and the sample needle 6 (removal and discharge device) are to be provided with a suitable controllable drive. The control can be realized by means of a control unit (not shown), which can be typically constructed as a microprocessor switch, which has available suitable control outputs and, if necessary, suitable signal inputs. The control can be performed via suitable software (firmware). Because known sample injectors also have available such a control unit, for upgrading an existing sample injector to form a combination sample injector/fraction collector according to the invention, in the simplest case, only one switch valve is exchanged and new software (firmware) is imported. Because such a control unit is known and the control unit for realizing the invention differs only in terms of functionality, the representation of the control unit in the drawing can be eliminated. The different features and properties of the control unit according to the invention relative to known control units can be defined through functional features.

As described above, the collected fractions should contain a defined, preset volume.

Without further measures, the liquid drop when it has reached such a size that it drips due to gravity, would then be led from the sample needle 6 into the fraction-collecting container 12. The critical drop size depends on many factors, such as the surface tension and specific mass of the liquid, as well as movements of the sample needle, therefore, the liquid volume actually deposited into the fraction-collecting containers 12 would greatly deviate.

The dripping can be realized according to the invention through different methods at the desired time. A few of these methods will be explained in more detail with reference to FIG. 4. FIG. 4 shows the following parts: a sample needle 6, one of the fraction-collecting containers 12, a liquid drop 70 at the end of the sample needle 6, a punch 71, and an air flow 72.

The simplest possibility for realizing the dripping of the liquid drop consists in moving the sample needle 6 so that the liquid drop 70 touches one of the walls of the fraction-collecting container 12. Here, it is especially useful to use sample-collecting containers 12 with downwardly tapering inner diameter, as shown in FIG. 4a. Such containers are frequently used as sample containers 7 and are therefore easily available. In this case, it is sufficient to lower the sample needle 6 far enough for the liquid drop 70 to touch the walls of the sample container 12. Because the walls have a significantly greater surface area than the sample needle 6, practically the entire liquid drop 70 then remains adhered in the fraction-collecting container 12, and also when the sample needle 6 is extracted again from the container.

Another method is shown in FIG. 4b. This method can be used in sample injectors, which have available a punch 71 with air flushing. The punch 71 is normally used to break through a cover possibly existing in the sample containers 7. Air flushing is normally used in such devices to clean the space between the sample needle 6 and the punch 71 from undesired liquid residue, e.g., sample material. For this purpose, an air flow 72 is introduced into the punch 71 and this air flow is discharged at the bottom between the sample needle 6 and the punch 71. According to the invention, however, the existing components are used not only for cleaning the space between the sample needle 6 and the punch 71 (here it involves the simple blowing of contaminants). Instead, with a defined air flow, which can be formed as a defined air pulse, the liquid drop detaches from the sample needle at a defined time. The course of the air pulse (time course of the flow rate) can be controlled by a control unit (not shown) in connection with a unit for generating the air pulse. In the simplest case, the control unit opens a controllable valve of a line, which is pressurized with air pressure and which is connected to the interior of the punch 71, only at the desired time.

This method and this device for dripping a drop of a liquid medium, especially a fraction, can obviously be used for any other fraction collecting devices or combination sample injecting and fraction collecting devices.

A third possibility for realizing the dripping process is a sudden movement of the sample needle 6, so that the liquid drop 70 cannot follow due to its inertia and thus drip into the fraction-collecting container 12.

Which of the mentioned methods is best suited depends on the conditions of the corresponding sample injector and on the size of the liquid drops to be fractioned.

If the volume to be collected per fraction is greater than the volume that a single drop can assume, the method just described must be applied only to the last drop.

In most cases, the collected fractions should be fed to a second separating step. For this purpose, in place of the original samples from the sample containers 12, now the already previously separated fractions are injected from the fraction-collecting containers 12.

Thus it is possible to perform two successive separating steps with the construction according to the invention.

For a two-dimensional separation with two successive separating steps, as a rule, the second separating step must be performed with a different column type, different solution compositions, and possibly also different flow rates.

The now two-dimensional, separated sample components available at the output of the column after the second separating step can now be fractioned again or fed directly to a detection device, for example, a UV detector or a mass spectrometer.

For such applications, for the construction according to the invention, as in the state of the art, another switch valve is necessary at the output of the column 20. This is not considered in FIG. 2 and FIG. 3 since these figures are used to show only the fractioning principle. Inventive arrangements making this process possible are described further below.

Because 8-port switch valves, as required for the solution according to the invention, are not specifically available on the market, it can be useful to use a 10-port valve in place of the 8-port valve.

Figure 5:
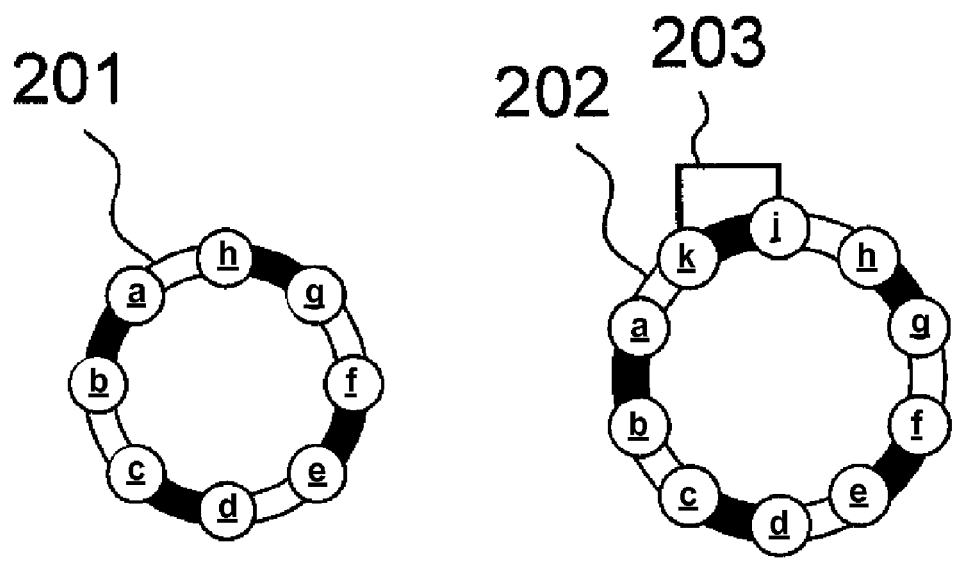
FIG. 5 is a schematic representation for explaining the use of a 10-port valve as a replacement for an 8-port valve.

This is possible without problem, as shown in FIG. 5. For the 10-port valve 202, the unnecessary ports j and k are interconnected by a so-called bridge 203. The other ports a to h now have in both positions the same functionality as the 8-port valve. The volume added between ports a and h does not disrupt the application according to the invention, because this path is otherwise needed only for emptying the dosing syringe 4 into the container for waste.

Because the costs for an 8-port or 10-port switch valve are only marginally higher than for a 6-port switch valve, the solution according to the invention means significant savings in terms of complication and costs. Neither an additional valve nor the associated control electronics are needed. In addition, in many cases subsequent conversion is possible, because the drive system of 6-port and 10-port valves is usually identical.

In terms of functionality, the invention relative to the state of the art signifies no restrictions, because fractioning must necessarily take place at a significantly later time than injection.

The devices needed for fixing a defined fraction volume are also already present in a normal sample injector. Due to the invention, an existing sample injector can be expanded with minimal conversion expense to form a combination sample injector/fraction collector.

As long as sufficient switch valves are available in the construction, the available switch valve can be used for realizing more complicated and more powerful arrangements, as described below.

As already explained, the embodiment shown in FIG. 3 (like the arrangement shown in FIG. 2 according to the state of the art) is used to explain the principle of the fractioning in the one-dimensional case. For the practical realization of at least two separating steps with 2 separating phases (2D separation), additional components are required. Below, embodiments based on the solution according to the invention are proposed that allow individual separating steps to be optimized essentially independently of each other.

Figure 6:
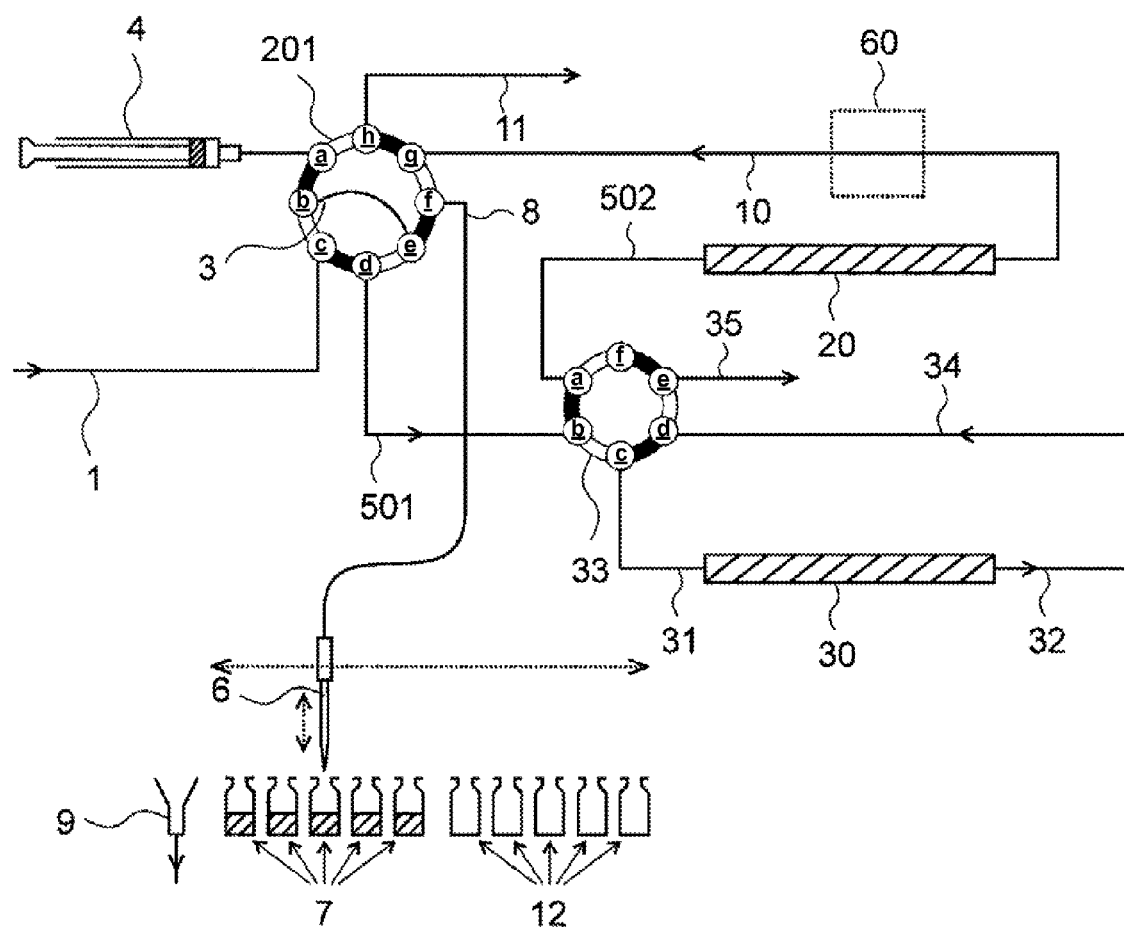
FIG. 6 is a schematic representation of another embodiment of a device according to the invention for 2D separation with fractioning according to the first dimension.

FIG. 6 shows an embodiment that allows a two-dimensional material separation (2D chromatography). Relative to the embodiment in FIG. 3, the following additional components were added: a second column 30, an input capillary 31 for the second column, an output capillary 32 for the second column, a column switch valve 33, an additional input capillary 34, an additional waste capillary 35, an optional detector 60 and connection capillaries 501 and 502.

The second column 30 is used for performing the second separating step. The flow agent for this is delivered from a second pump via the additional input capillary 34. The column switch valve 33 can lead the liquid flow coming from the capillary 501 either via the column 20 or via the column 30.

In the shown position of the column switch valve 33 (switch position a-b), the function of the arrangement corresponds exactly to the arrangement according to FIG. 3. The sample is separated by the column 20 and the fractions are collected in the fraction-collecting containers 12. This process can be monitored or controlled with the optional detector 60.

For the separation in the second dimension, a second column 30 is used. The solution flow for this second column is delivered via the capillary 34. The use of a second column and a second solution flow has the advantage that column packing materials, solutions, and flow rates that are different from the first and the second separating step can be used. Therefore, for the second separating step, different material properties can be exploited than for the first separating step, which is designated as 2D chromatography. In this way, an especially efficient separation of complex material mixtures is possible.

For the second separating step, one of the collected fractions is removed from the corresponding fraction-collecting container 12 and injected in the way described above. The column switching valve 33 is switched to position f-a and advances the fraction to the second column 30. For the preferred selection of the solution and the column packing material, the fraction first remains suspended from the head of the second column 30. For the actual separation, the column switch valve is brought back into position a-b. The solution fed via the additional input capillary 34 causes the separating process, i.e., the individual components of the fraction pass through the column 30 at different speeds and are made available at the output capillary 32 in time-separated form. A detection device, for example, a UV detector and/or a mass spectrometer, with which the material quantity and/or material composition can be determined, can be connected there.

The entire second separating process is performed in series for all of the fractions to be analyzed, which are located in the fraction-collecting containers.

The time profile of the separations of the individual samples can be selected differently.

One possibility is to first perform the first separating step in series for all of the samples 7 to be analyzed and to buffer the resulting fractions in a corresponding number of fraction-collecting containers 12. Then the second separating step is performed for all of the collected fractions.

As a second possibility, a sample 7 is first separated into fractions in the first separating step and then the second separating step is applied to these fractions. Only then is the next sample injected and processed accordingly.

The arrangement shown in FIG. 6 consequently allows a two-dimensional separation of a mixture, wherein, overall, only two switch valves are needed. Analogous to FIG. 5, constructions with a higher number of ports can also be used for the switch valves.

Figure 7:
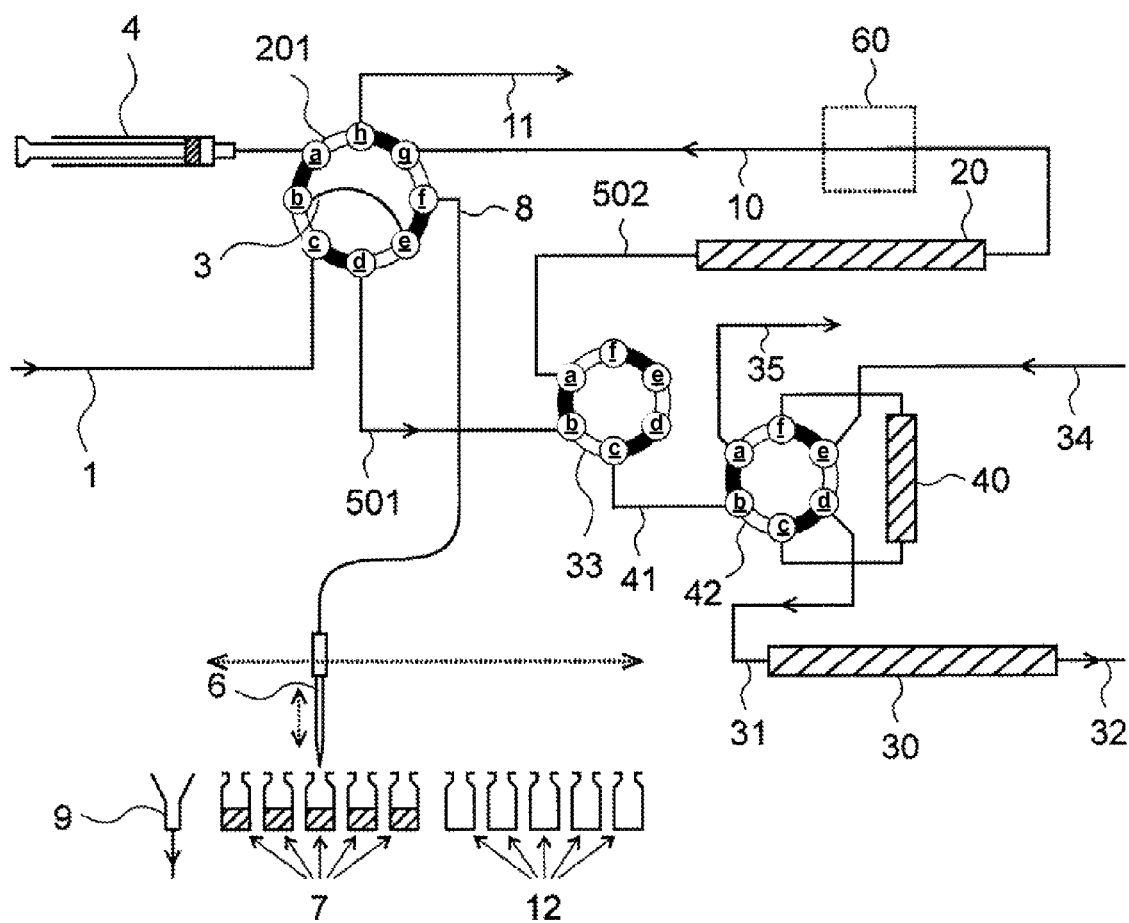
FIG. 7 is a schematic representation of another embodiment of a device according to the invention for 2D separation with trap columns.

FIG. 7 shows another application based on the invention, in which a trap column 40 for realizing a "reversed phase" separation is connected before the second column 30. Relative to the embodiment according to FIG. 3, the following additional components were added: a second column 30, an input capillary 31 for the second column, an output capillary 32 for the second column, a column switch valve 33, a connection capillary 41, a trap column switch valve 42, an additional input capillary 34, an additional waste capillary 35, an optional detector 60, and connection capillaries 501 and 502.

The structure and the function correspond to FIG. 6, but now a trap column 40 with trap column switch valve 42 is connected before the second column 30.

In the shown position of the column switch valve 33 (position a-b), the function of the arrangement corresponds, in turn, exactly to the arrangement according to FIG. 3. The fractions are collected in the fraction-collecting containers 12. With the optional detector 60, this process can be monitored or controlled.

For the separation in the second dimension, here a second column 30 is also used. The solution flow for this second column is delivered via the capillary 34. This has the same advantages as described above.

For the second separating step, one of the collected fractions is removed from the corresponding fraction-collecting container 12 and injected in the way described above. The column switch valve 33 and the trap column switch valve 42 are both switched to position f-a. The fraction is thus led via the connection capillary 501, the column switch valve 33, and the trap column switch valve 42 to the trap column 40. For a preferred selection of the column packing materials and the solution, the sample remains suspended from the input of the trap column 40 (bottom connection in FIG. 7) where it becomes concentrated. Then the trap column switch valve 42 is switched to switch position a-b. In this way, the solution flow supplied via the additional input capillary 34 is led in the reverse direction through the trap columns and also via the trap column switch valve 42 to the second column 30. For a preferred selection of the solution and column packing materials, the concentrated fraction is transported to the column 30 and separated there, i.e., the individual components of the fraction pass through the column 30 at different speeds and become available at the output capillaries 32 in time-separated form. A detection device, for example, a UV detector and/or a mass spectrometer, with which the material quantity and/or the material composition can be determined, can be connected there.

The entire second separating device is performed in series for all of the fractions to be analyzed, which are located in the fraction-collecting containers.

The advantage of using a trap column is that the sample material, in contrast to the solution, does not pass through the trap column and thus cannot be concentrated. The sample volume is therefore reduced and the concentration is increased. For low-concentration samples, this is a prerequisite for good separation. Because a certain diluting of the samples cannot be avoided due to the fractioning, the use of a trap column in connection with the fractioning is especially advantageous.

Figure 8:
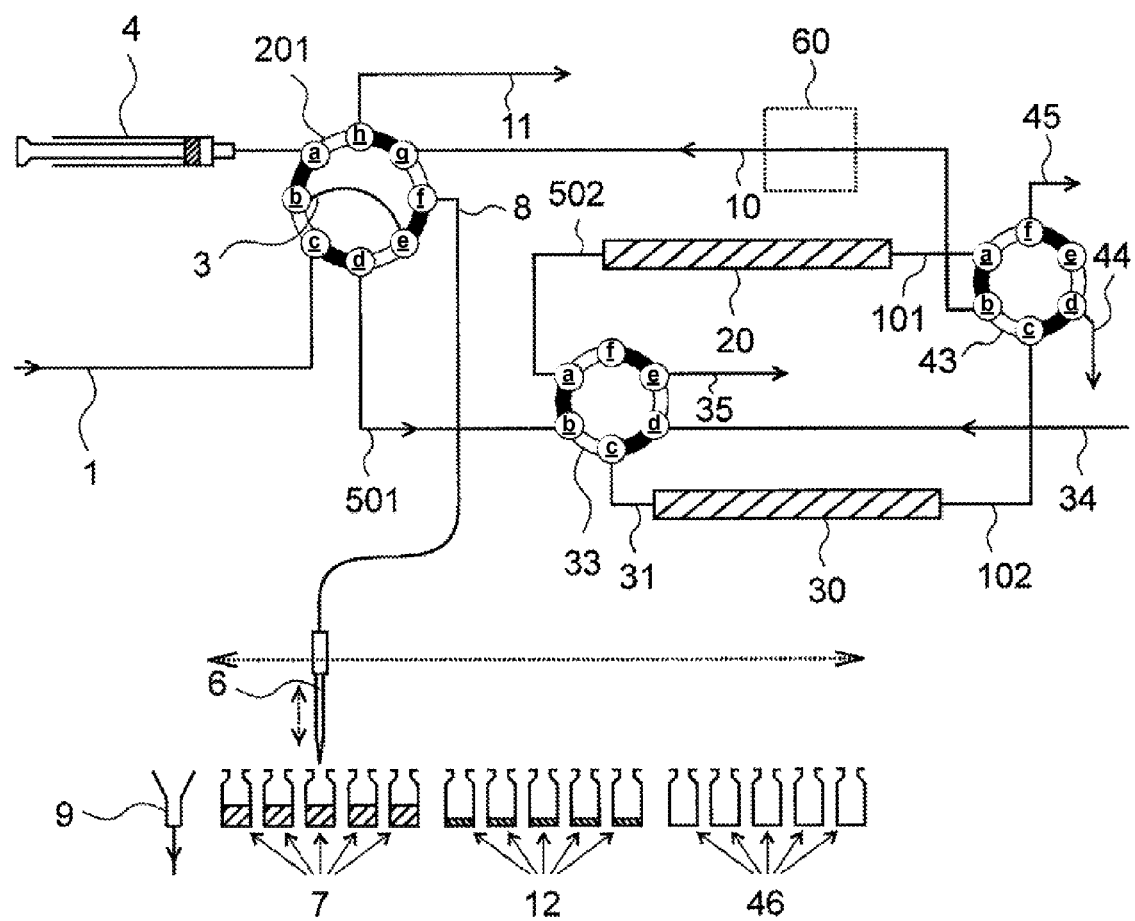
FIG. 8 is a schematic representation of another embodiment of a device according to the invention for 2D separation with fractioning according to both dimensions.

Through the expansion of the construction from FIG. 6 shown in FIG. 8 by a second column switch valve, the sample components separated in the second separation step can again be fractioned. Relative to the embodiment according to FIG. 6, the following additional components were added: connection capillaries 101 and 102, a second column switch valve 43, waste capillaries 44 and 45, and additional fraction-collecting containers 46.

The construction and the function correspond to the embodiment from FIG. 6, but the outputs of the two columns 10 and 30 are connected to a second column switch valve 43. Here, the separating products can be selectively switched from column 20 or from column 30 to the return capillary and thus fractioned.

In the shown position of the second column switch valve 43 (position a-b), the function of the arrangement corresponds exactly to the arrangement according to FIG. 6. The fractions are collected in the fraction-collecting containers 12. This process can be monitored or controlled with the optional detector 60.

The separation in the second dimension is performed, in turn, with the second column 30 and the solution flow, which is delivered via the capillary 34. Here, however, the second column switch valve 43 is switched to position f-a, so that now the output of the second column 30 is connected to the return capillary 10 via the connection capillary 102 and the second column switch valve 43. As a sample for this second separating step, each of the fractions collected previously in the fraction-collecting containers 12 from the first separating step are used.

These are further separated in the second separating step by the column 30 and reach the sample needle 6 via the return capillary 10, the switch valve 202, and the connection capillary 8. For new fractioning, this is positioned on the additional fraction-collecting containers 46, which hold the twice-fractioned sample components.

The arrangement shown in FIG. 8 consequently allows a two-dimensional separation of a mixture with fractioning of the two-dimensional, separated components, wherein, overall, only three switch valves are needed. Analogous to FIG. 5, construction with a higher number of ports can also be used for the switch valves.

The above described preferred embodiments are intended to illustrate the principles of the invention, but not to limit the scope of the invention. Various other embodiments and modifications to these preferred embodiments may be made by those skilled in the art without departing from the scope of the present invention.

The invention claimed is:

1. A device for feeding samples to a separating device and for collecting sample fractions generated by means of the separating device, especially for high-performance liquid chromatography, the device comprising:
(a) a first switch valve unit, which has at least eight ports and two switch positions,
  (i) wherein, in a first switch position, first selected pairs of the ports are interconnected, and
  (ii) wherein, in a second switch position, second selected pairs of the ports that are not interconnected in the first switch position are interconnected;
(b) a dosing device for feeding a sample to the first switch valve unit, which is connected to a suction port of the first switch valve unit, and
(c) which is adapted to interact with a removal and discharge device for removing a sample from at least one sample-holding container and for discharging a fraction into one of several fraction-holding containers, the removal and discharge device being connected to a suction and discharge port of the first switch valve unit;
(d) wherein a solution feed port of the first switch valve unit is adapted to be connected to a feed line for a first solution;
(e) wherein a first separating device transfer port of the first switch valve unit is adapted to be connected to an input port of the separating device, and a second separating device transfer port of the first switch valve unit is adapted to be connected to an output port of the first separating device;
(f) wherein a first port of a sample reservoir is connected to a first sample reservoir port of the first switch valve unit, and a second port of the sample reservoir is connected to a second sample reservoir port of the first switch valve unit;
(g) wherein a waste port of the first switch valve unit can be connected to a container for waste of the first switch valve unit; and
(h) wherein the ports of the first switch valve unit are assigned so that
  (i) in the first switch position, the suction port and the first sample reservoir port are interconnected, the solution feed port and the first separating device transfer port are interconnected, the second sample reservoir port and the suction and the removal and discharge port are interconnected, and also the second separating device transfer port and the waste port are interconnected; and
  (ii) in the second switch position, the first sample reservoir port and the solution feed port are interconnected, the first separating device transfer port and the second sample reservoir port are interconnected, the suction and discharge transfer port and the separating device transfer port are interconnected, and also the waste port and the suction port are interconnected.

2. The device of claim 1, wherein the first switch valve unit is constructed as a 10-port switch valve unit and that two additional ports are short-circuited by means of a bridge line.

3. The device of claim 1, wherein the first switch valve unit has a controllable drive and a control unit which is adapted to control the drive, so that:
(a) the first switch valve unit is located in the first switch position during a sample suction phase, wherein the sample is transported from one of several sample-holding containers into the sample reservoir, by means of the removal and discharge device during the sample suction phase;
(b) the first switch valve unit is set to the second switch position after the sample suction phase, wherein, in a sample injection phase following the sample suction phase, the sample is fed to the first separating device from the sample reservoir via the separating device transfer port by means of a solution fed via the solution feed port and a medium fed to the removal and discharge device from the first separating device via the separating device transfer port or contained in the removal and discharge device is fed to a waste port;
(c) after the sample injection phase, the first switch valve unit is set to the first switch position or remains in the second switch position, wherein in the first switch position solvent is fed directly to the first separating device and medium that is fed to the separating device transfer port is fed by way of the waste port of the first switch valve unit to a waste reservoir, and in the second switch position solvent is fed through the intermediary of the sample reservoir to the first separating device and medium that is fed to the separating device transfer port is fed by way of the suction and discharge port of the first switch valve unit to the removal and discharge device and from the latter to the additional waste port, and
(d) the first switch valve unit is set to the second switch position before the separated fractions appear at the separating device transfer port, wherein in a first separating phase, additional solution is fed to the first separating device, and the medium fed from the output port of the first separating device to the separating device transfer port of the first switch valve unit is fed to the removal and discharge device via the suction and discharge port of the first switch valve unit and discharged from this removal and discharge device in the form of several fractions each into a fraction-holding container.

4. The device of claim 3, wherein the control unit is adapted to set the removal and discharge device and/or the sample-holding container, from which the sample is to be removed, in a position from which a sample can be removed from the desired sample-holding container before the sample suction phase.

5. The device of claim 3, wherein the control unit is adapted to move the removal and discharge device and/or a waste port into a position during the injection phase from which the medium discharged from the removal and discharge device is fed to the waste port.

6. The device of claim 3, wherein the control unit is adapted to successively set the removal and discharge device and/or the fraction-holding containers into several fraction discharge positions, wherein, in each fraction discharge position, medium discharged from the removal and discharge device is fed as a fraction to the relevant fraction-holding container.

7. The device of claim 1, wherein between the separating device transfer port of the first switch valve unit and the input port of the first separating device there is a second switch valve unit, which in a first switch position connects the separating device transfer port of the first switch valve unit with the input port of the first separating device, and in a second switch position connects the separating device transfer port of the first switch value unit to an input port of a second separating device for a second separating phase.

8. The device of claim 7, further comprising a sample-concentrating unit connected between the input port of the second separating device and the second switch valve unit.

9. The device of claim 8, wherein the control device is adapted to control the switch valves and the removal and discharge device, so that for each sample, initially the first separating phase is performed and then for each fraction of the first sample, a second separating phase is performed.

10. The device of claim 8, wherein the sample-concentrating unit further comprises a retaining unit and a third switch valve unit, wherein the retaining unit and the third switch valve unit are connected so that in a second switch position of the third switch valve unit, the medium guided in the direction towards the second separating device and containing the sample is led through the retaining unit, wherein the retaining unit allows the passage of essentially only the solution and the blocks the components of the sample, and wherein, in a first switch position a second solution fed to the sample-concentrating unit flows through the retaining unit in the reverse direction, which flushes sample components concentrated on the retaining unit and transports them to the second separating device.

11. The device of claim 10, wherein the third switch valve unit has a controllable drive, and wherein the control unit is adapted to control the third switch valve unit so that during the sample injection phase, the third switch valve unit is set to the second switch position and the second switch valve unit is set to the second switch position, and wherein in the second separating phase following the sample injection phase, the third switch valve unit is set to the first switch position.

12. The device of claim 10, wherein a fourth switch valve unit is provided, which connects, in a first switch position, the output port of the first separating device and, in a second switch position, the output port of the second separating device to the separating device transfer port of the first switch valve unit.

13. The device of claim 12, wherein the fourth switch valve unit has a controllable drive, and in which the control unit is adapted to control the fourth switch valve unit so that it is set to the first switch position during the first separating phase and to the second switch position during the second separating phase.

14. The device of claim 12, wherein the control unit is adapted to successively set the removal and discharge device and/or the fraction-holding containers to several fraction discharge positions during the second separating phase, wherein in each fraction discharge position, medium discharged from the removal and discharge device is fed to the relevant fraction-holding container as a fraction.

15. The device of claim 7, wherein the second switch valve unit has a controllable drive, and wherein the control unit is adapted to set the second switch valve unit into the second switch position for performing the second separating phase.

16. The device of claim 15, wherein the control unit is adapted to control the drive of the first switch valve unit for performing the second separating phase, so that:
(a) the first switch valve unit is located in the first switch position during a sample suction phase for the second separating phase, wherein the sample is transported from a fraction-holding container into the sample reservoir by means of the removal and discharge device during the sample suction phase; and
(b) the first switch valve unit is set to the second switch position after the sample suction phase, wherein in a sample injection phase for the second separating phase following the sample suction phase, the sample is fed from the sample reservoir to the second separating device via the separating device transfer port and the second switch valve unit by means of the solution fed via the solution feed port.

17. The device of claim 15, wherein the second switch valve unit has at least six ports and two switch positions, and wherein:
(a) in the first switch position for the second switch valve unit, first selected pairs of the second switch valve unit ports are interconnected;
(b) in the second switch position for the second switch valve unit, second selected pairs of the second switch valve unit ports that are not interconnected in the first switch position, are interconnected; and
(c) the separating device transfer port of the first switch valve unit is connected to a sample injection port of the second switch valve unit and a separating device transfer port of the second switch valve unit is adapted to be connected to a second separating device;
(d) a passage port of the second switch valve unit is adapted to be connected to the input port of the first separating device;
(e) a solution feed port of the second switch valve units adapted to be connected to a feed line for a second solution; and
(f) the ports of the second switch valve unit are assigned so that:
(i) in the first switch position, the passage port is connected to the sample injection port and the separating device transfer port is connected to the solution feed port; and
(ii) in the second switch position, the sample injection port is connected to the separating device transfer port and the solution feed port is connected to a waste port of the second switch valve unit.

18. The device of claim 15, wherein the control unit is adapted to control the drives of the first and second switch valve units for performing a second separating phase such that:
(a) the first switch valve unit is located in the first switch position during a sample suction phase, wherein a sample is transported from a fraction-holding container into the sample reservoir by means of the removal and discharge device during the sample suction phase;
(b) after the sample suction phase, the first switch valve unit is set to the second switch position and the second switch valve unit is set to the second switch position, wherein in a sample injection phase following the sample suction phase, the sample is fed from the sample reservoir to the sample injection port of the second switch valve unit via the separating device transfer port of the first switch valve unit by means of the solution fed via the solution feed port of the first switch valve unit and is fed to the input port of the second separating device via the separating device transfer port of the second switch valve unit; and
(c) after the sample injection phase, the second switch valve unit is set back to the first switch position, so that the second solution is fed to the input port of the second separating device via the solution feed port of the second switch valve unit and the separating device transfer port of the second switch valve unit.

* * * * *